United States Patent
Keil

(10) Patent No.: US 9,475,044 B2
(45) Date of Patent: Oct. 25, 2016

(54) TEST STRIP WITH A SHAPED TIP FOR SKIN STRAIGHTENING

(75) Inventor: Michael Keil, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 790 days.

(21) Appl. No.: 13/273,409

(22) Filed: Oct. 14, 2011

(65) Prior Publication Data

US 2012/0035506 A1  Feb. 9, 2012

Related U.S. Application Data

(62) Division of application No. 12/544,296, filed on Aug. 20, 2009, now Pat. No. 8,061,004.

(51) Int. Cl.
*G01N 31/22* (2006.01)
*B01L 3/00* (2006.01)
(Continued)

(52) U.S. Cl.
CPC ............ *B01L 3/5023* (2013.01); *A61B 5/1411* (2013.01); *A61B 5/1519* (2013.01); *A61B 5/150022* (2013.01); *A61B 5/150068* (2013.01); *A61B 5/150282* (2013.01); *A61B 5/150358* (2013.01); *A61B 5/150435* (2013.01); *A61B 5/150503* (2013.01); *B01L 3/502715* (2013.01); *A61B 5/157* (2013.01); *B01L 2300/0825* (2013.01);
(Continued)

(58) Field of Classification Search
CPC .......... G01N 2021/7759; G01N 2035/00208; G01N 2035/00128; G01N 2201/0256; G01N 33/4875; A61B 5/150358; A61B 5/15165; B01L 2300/0825; B01L 3/50855

USPC ........................................................ 422/404
See application file for complete search history.

(56) References Cited

U.S. PATENT DOCUMENTS 6,132,449 A    10/2000  Lum et al.
6,207,000 B1 *  3/2001  Schwobel ............. B01L 3/5023
                                                  156/248

(Continued)

FOREIGN PATENT DOCUMENTS

WO    WO 2006/037646 A2    4/2006

OTHER PUBLICATIONS

China Patent Application No. 201080036799.X Search Report mailed Sep. 3, 2013.
(Continued)

*Primary Examiner* — Jill Warden
*Assistant Examiner* — Brittany Fisher
(74) *Attorney, Agent, or Firm* — Woodard, Emhardt, Moriarty, McNett & Henry LLP

(57) ABSTRACT

The test strip stabilizes skin prior to incision by a lancet tip. The innovative test strip includes a pair of skin contacting tabs that apply pressure linearly to the skin to stretch the skin taut. Beneficially an incision by a lancet tip to an accurate depth can be formed on the taut skin. Moreover, pressure from the tabs is applied linearly to the skin which results in a higher ratio of pressure to surface that can be reached as compared to applying pressure laminarily to skin. Some manufacturing techniques of the skin contacting tabs include cutting or stamping through all of the layers and test area of the test strip to form these tabs. These techniques increase the manufacturing efficiency and cost savings associated with test strips and integrated lancet testing devices. Contamination from other sampling events is eliminated since the test strips are disposed of after each use.

12 Claims, 6 Drawing Sheets

(51) Int. Cl.
*A61B 5/15* (2006.01)
*A61B 5/151* (2006.01)
*G01N 33/52* (2006.01)
*A61B 5/157* (2006.01)

(52) U.S. Cl.
CPC ..... *Y10T 29/49789* (2015.01); *Y10T 29/49798* (2015.01); *Y10T 29/49885* (2015.01); *Y10T 156/1052* (2015.01)

(56) References Cited

U.S. PATENT DOCUMENTS

| | | | |
|---|---|---|---|
| 6,258,075 B1 | 7/2001 | Taylor et al. | |
| 6,306,152 B1 | 10/2001 | Verdonk et al. | |
| 6,561,989 B2 | 5/2003 | Whitson | |
| 7,299,081 B2 | 11/2007 | Mace et al. | |
| 7,351,212 B2 | 4/2008 | Roe | |
| 7,476,202 B2 | 1/2009 | Raney et al. | |
| 7,481,777 B2* | 1/2009 | Chan et al. | 600/583 |
| 7,815,579 B2 | 10/2010 | Roe | |
| 7,935,063 B2 | 5/2011 | Roe | |
| 2002/0168290 A1 | 11/2002 | Yuzhakov et al. | |
| 2003/0146110 A1* | 8/2003 | Karinka | G01N 27/3272 205/777.5 |
| 2004/0127818 A1 | 7/2004 | Roe | |
| 2004/0127929 A1 | 7/2004 | Roe | |
| 2004/0138688 A1 | 7/2004 | Giraud | |
| 2004/0236251 A1 | 11/2004 | Roe et al. | |
| 2005/0019212 A1* | 1/2005 | Bhullar | G01N 27/3272 422/400 |
| 2005/0283094 A1 | 12/2005 | Thym et al. | |
| 2006/0131171 A1* | 6/2006 | Kobayashi | 204/403.01 |
| 2006/0200045 A1 | 9/2006 | Roe | |
| 2007/0149897 A1* | 6/2007 | Ghesquiere et al. | 600/583 |
| 2007/0167869 A1 | 7/2007 | Roe | |
| 2007/0173739 A1* | 7/2007 | Chan | 600/583 |
| 2007/0173740 A1* | 7/2007 | Chan et al. | 600/583 |
| 2007/0278097 A1* | 12/2007 | Bhullar | B29C 66/4722 204/403.01 |
| 2008/0060424 A1* | 3/2008 | Babic | B01L 3/5023 73/61.41 |
| 2008/0147107 A1 | 6/2008 | Roe et al. | |
| 2008/0208078 A1 | 8/2008 | Neel et al. | |

OTHER PUBLICATIONS

International Application No. PCT/EP2010/005057 International Search Report and Written Opinion, mailed Feb. 14, 2011.

* cited by examiner

TEST STRIP WITH A SHAPED TIP FOR SKIN STRAIGHTENING

CROSS REFERENCE TO RELATED APPLICATIONS

This application is a divisional of U.S. patent application Ser. No. 12/544,296 filed Aug. 20, 2009 now U.S. Pat. No. 8,061,004, which is hereby incorporated by reference.

BACKGROUND

It is beneficial to stabilize the skin near an incision site prior to forming an incision so that a lancet tip can form an incision to an accurate depth. However, the condition of skin has a significant effect on how it is punctured by a lancet tip and the associated pricking depth of the lancet tip. For example, elasticity of skin is variable for each patient and from site to site on a patient's body. Moreover, before a lancet tip can form an incision in skin to a certain depth, the skin must be pulled taut enough to smooth out the skin and exceed the puncture threshold before the lancet can penetrate the skin. If the skin of a patient is not pulled taut prior to forming the incision, then the lancet tip must stretch the skin to make it taut prior to forming an incision. Therefore the lancet may not form an incision to an accurate depth.

Typically the minimal parts for an integrated body fluid sampling device include a test strip and a lancet. As can be appreciated there is a cost associated with manufacturing the components of integrated body fluid sampling devices such as test strips, lancets, and housings. Therefore forming an additional mechanism to stabilize skin typically increases the manufacturing cost of body fluid sampling devices. Thus, there is a need to reduce the manufacturing costs associated with a body fluid sampling device.

Thus, there is a need for improvement in this field.

SUMMARY

The test strip described herein addresses the issue of stabilizing the skin near an incision site. Stabilization of the skin near an incision site is accomplished with a uniquely shaped sampling end of a test strip that contacts and stabilizes skin near the incision site prior to an incision being formed in skin. Moreover, the unique shape of the sampling end of the test strip also stretches the skin near the incision site prior to contact by a lancet tip. The inventor has found that specific dimensions of the uniquely shaped sampling end of the test strip optimize stabilization and stretching of skin prior to an incision being formed. The test strip described herein also increases manufacturing efficiencies and cost savings associated with test strips and integrated lancet testing devices.

Some body fluid sampling devices define an opening at the end of a housing that is pressed against skin to cause the skin to bulge within the opening. The opening of the housing typically surrounds the incision site and applies pressure laminarily against the skin. Comparatively, the unique shape of the sampling end of the test strip described herein applies a substantially linear force or pressure against the skin. The inventor has found that applying a linear pressure results in a higher ratio of pressure to surface can be reached when a user presses the sampling end of the test strip against skin as compared to laminarily applying pressure to skin.

Yet another problem often associated with a mechanism on the end of a housing of a body fluid sampling device for applying pressure to skin is the potential for contamination from one body fluid sampling event to the next subsequent one. As can be appreciated the uniquely shaped test strip disclosed hereafter is disposed of after use thereby eliminating the potential for contamination from one body fluid sampling event to the next one.

Some or all of the above mentioned features may be present in the corresponding independent or dependent claims, but should not be construed to be a limitation unless expressly recited in a particular claim. This summary is provided to introduce a selection of the concepts that are described in further detail in the detailed description and drawings contained herein. This summary is not intended to identify any primary or essential features of the claimed subject matter, nor is it intended to be used as an aid in determining the scope of the appended claims. Each embodiment described herein is not intended to address every object described herein, and each embodiment does not include each feature described. Other forms, embodiments, objects, advantages, benefits, features, and aspects of the present invention will become apparent to one of skill in the art from the detailed description and drawings contained herein.

DESCRIPTION OF THE SELECTED EMBODIMENTS

Figure 1:
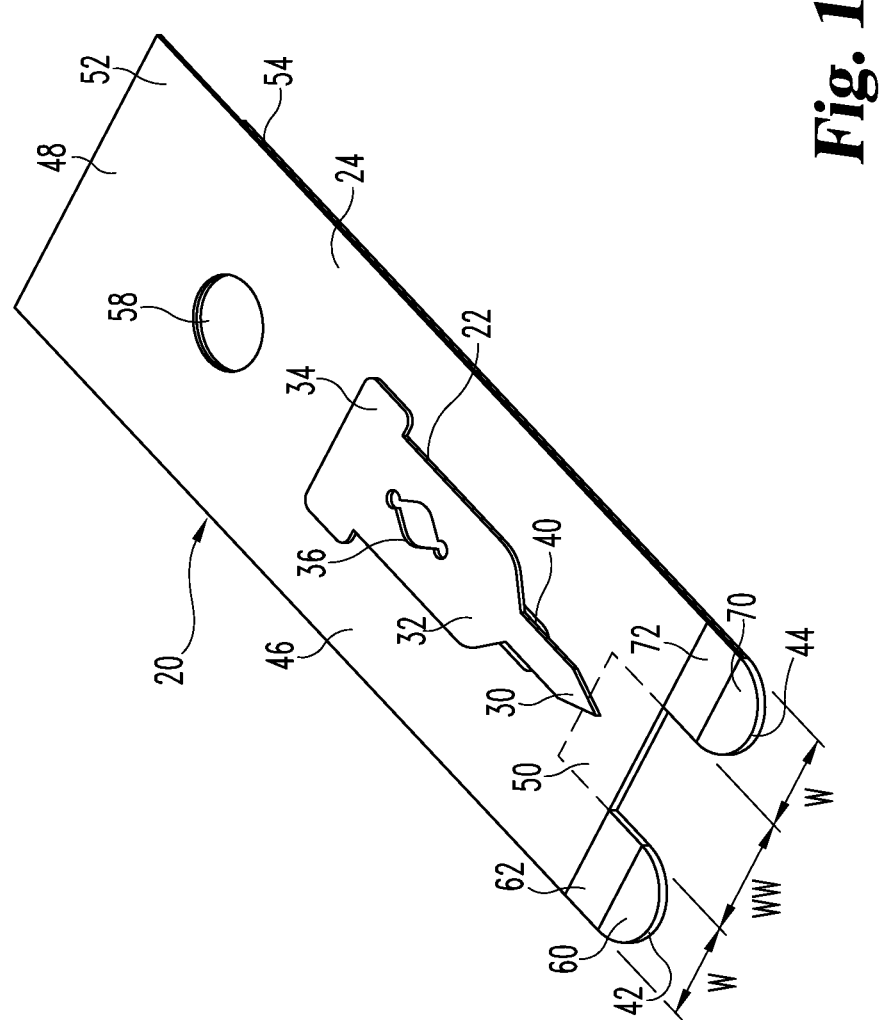
FIG. 1 is a top perspective view of an integrated lancet testing device.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 2:
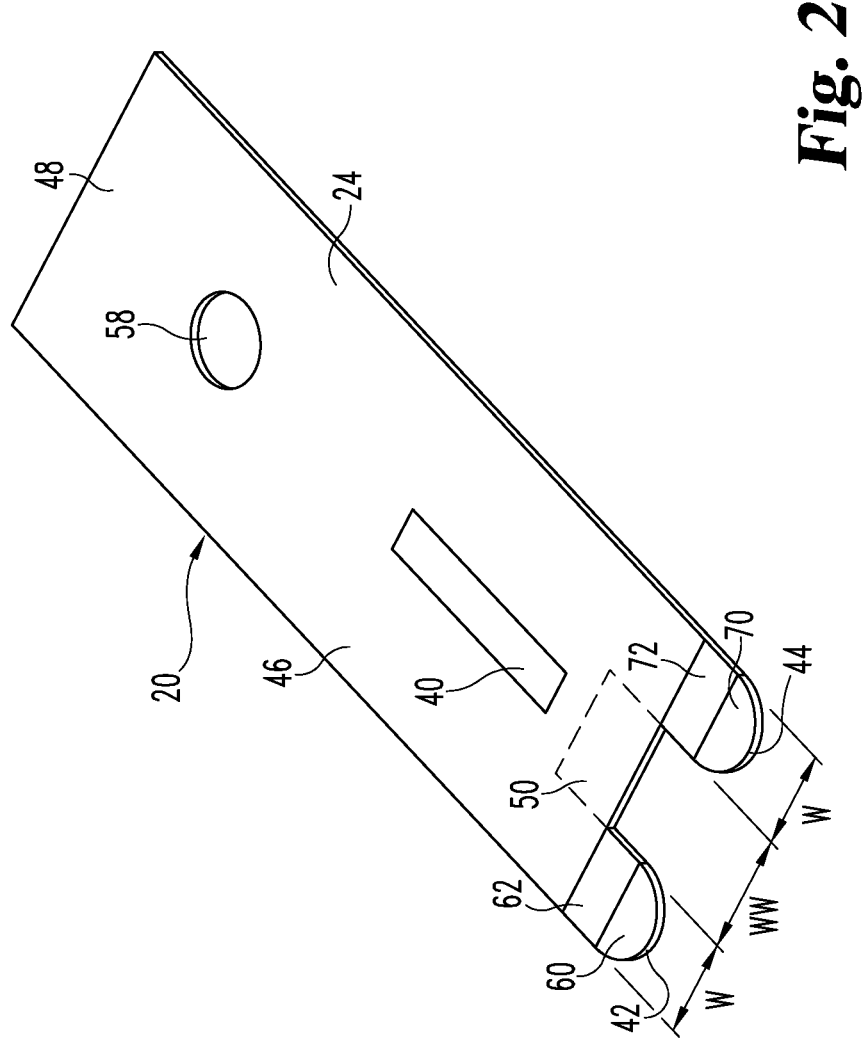
FIG. 2 is a back perspective of the FIG. 1 device with the lancet.
Figure 3:
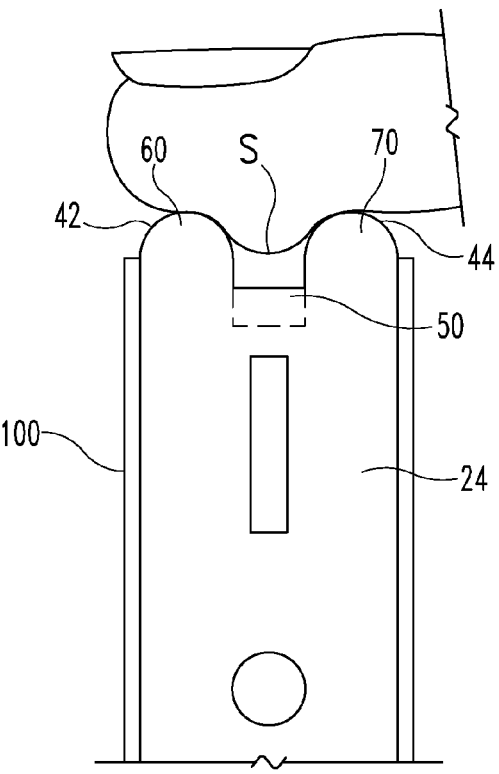
FIG. 3 is a back view of the FIG. 2 device extending from a housing with the FIG. 2 device pressed against a finger of a user.

An integrated lancing test strip 20 according to one embodiment will described with reference to FIGS. 1, 2, and 3. Integrated lancing test strip 20 is also commonly referred to as a lancet integrated test strip or "LIT" for short. Integrated lancing test strip 20 is configured to stabilize the skin near an incision site, form an incision in skin, collect a body fluid sample from the incision, and analyze the body fluid sample. Referring to FIG. 1, the integrated lancing test strip 20 includes a lancet or incision forming member 22 for forming an incision in tissue and a test strip 24. Both the lancet 22 and the test strip 24 are substantially flat such that the integrated lancing test strip 20 has an overall flat appearance. Since the general overall appearance of the integrated lancing test strip 20 is flat, multiple integrated lancing test strips 20 can be incorporated into magazines, cassettes, drums, cartridges and the like, which allows a plurality of integrated lancing test strips 20 to be stacked upon one another in a magazine or rolled around a reel in a cassette. As described in more detail below, the substantially flat shape of the integrated lancing test strip 20 allows the test strip 24 to be manufactured with a continuous process in which layers of component materials can be layered to form contiguous strips of test strips 24 that can be cut to form individual test strips. Moreover, the layers of materials and the test chemistry or reagent that form test strips 24 can be cut or stamped to form a first skin contacting tab 42 and a second skin contacting tab 44 in each test strip 24.

As can be seen in FIG. 1, the lancet 22 has a lancet tip 30 connected to a lancet body 32. The lancet 22 also includes a lancet end portion 34 connected to lancet body 32. The lancet body 32 defines a guide opening 36 sized to receive a driver configured to engage the guide opening 36 to move the lancet 22 to form an incision in skin. When the lancet 22 is attached to the test strip 24, the guide opening 36 is aligned with a depth limiting opening 40 in test strip 24, as described in more detail below. Additional details about a driver and other types of firing mechanisms are provided in U.S. patent application Ser. No. 11/070,502, filed Mar. 2, 2005 entitled "Dynamic Integrated Lancing Test Strip With Sterility Cover", now U.S. Pat. No. 7,815,579, and U.S. patent application Ser. No. 11/551,414, filed Oct. 20, 2006 entitled "System And Method For Breaking a Sterility Seal To Engage A Lancet", now U.S. Pat. No. 7,935,063, which are hereby incorporated by reference.

In the illustrated embodiment, the test strip 24 is an electrochemical type test strip. In one form, the test strip 24 includes a modified version of an ACCU-CHEK® brand test strip (Roche Diagnostics GmbH, Mannheim, Germany), but it is envisioned that other types of test strips can be used. For example, the test strip 24 in other embodiments can include an optical type test strip or can analyze fluid samples in other manners. As can be seen in FIGS. 1 and 2, the test strip 24 includes a first skin contacting tab 42 and a second skin contacting tab 44. The test strip 24 also includes a mid-portion 46 connected to the first skin contacting tab 42 and the second skin contacting tab 44. The test strip 24 includes an end portion 48 connected to the mid-portion 46. The mid-portion 46 defines a depth limiting opening 40 sized to receive a portion of a driver and/or opening 40 is sized for engagement with a gripper. In one embodiment, the opening 40 is a slot sized to receive a lancet gripper device. The test strip 24 includes a test area 50 positioned between the first skin contacting tab 42 and the second skin contacting tab 44. The test area 50 is designed to allow body fluid to move from an incision in skin up the test area 50 via capillary action. The test area 50 includes a reagent and is disposed between a first panel 52 and a second panel 54 and extends to a front edge of the first panel 52 and the second panel 54. The first panel 52 is laminated to the second panel 54. First panel 52 and second panel 54 can be continuous sheets of material that are laminated together to form contiguous strips of test strips 24. These contiguous strips of test strips 24 can be cut to form a plurality of individual test strips 24. In one embodiment, the front edge of the first panel 52 and the second panel 54 are cut to form the first skin contacting tab 42 and the second skin contacting tab 44. In another embodiment, the front edge of the first panel 52 and the second panel 54 are stamped to form the first skin contacting tab 42 and the second skin contacting tab 44. End portion 48 defines an opening 58 sized to attach or fix the test strip 24 to a test meter, a testing device, or a driver.

The first skin contacting tab 42 has a skin contacting portion 60 that is configured to contact skin near an incision site. As illustrated, skin contacting portion 60 is semi-circular in shape. The first skin contacting tab 42 also includes a leg portion 62 next to the skin contacting portion 60. The second skin contacting tab 44 includes a skin contacting portion 70 that is configured to contact skin near an incision site. The skin contacting portion 70 is semi-circular in shape. Skin contacting portion 60 and skin contacting portion 70 can be shaped the same or different from each other. The second skin contacting tab 44 includes a leg portion 72 next to skin contacting portion 70. In one embodiment, skin contacting portion 60 and skin contacting portion 70 each have a radius of approximately 1.625 millimeters and leg portion 62 and leg portion 72 each have a width, W, of approximately 3.25 millimeters. Moreover test area 50 has a width, WW, of approximately 2.5 millimeters. In one embodiment, the test strip 24 has a thickness of about 0.4 to 0.8 millimeters.

The operation of the integrated lancing test strip 20 according to one embodiment will now be described with reference to FIGS. 1, 2, and 3. FIG. 3 illustrates the position of the test strip 24 in relation to skin S prior to an incision being formed in skin S. Test strip 24 is positioned in a housing 100. Housing 100 can also be configured to contact skin S. As shown, first skin contacting portion 60 and second skin contacting portion 70 are pressed against skin S. As shown, skin S is stretched between first skin contacting portion 60 and second skin contacting portion 70. Additionally, skin S between first skin contacting portion 60 and second skin contacting portion 70 is bulged towards test area 50 to express a bodily fluid sample. First skin contacting portion 60 and second skin contacting portion 70 are sized so as to not apply force to skin S that will close an incision once it is formed. Next an incision in skin S is formed with lancet tip 30. Lancet tip 30 pierces skin S without depressing skin S between first skin contacting portion 60 and second skin contacting portion 70 because skin S is pulled taut. Therefore an incision in skin S can be formed to an accurate depth. The test area 50 is configured to collect a body fluid sample via capillary action. After the body fluid sampling event is complete, the used and contaminated integrated lancing test strip 20 is disposed of.

Figure 7:
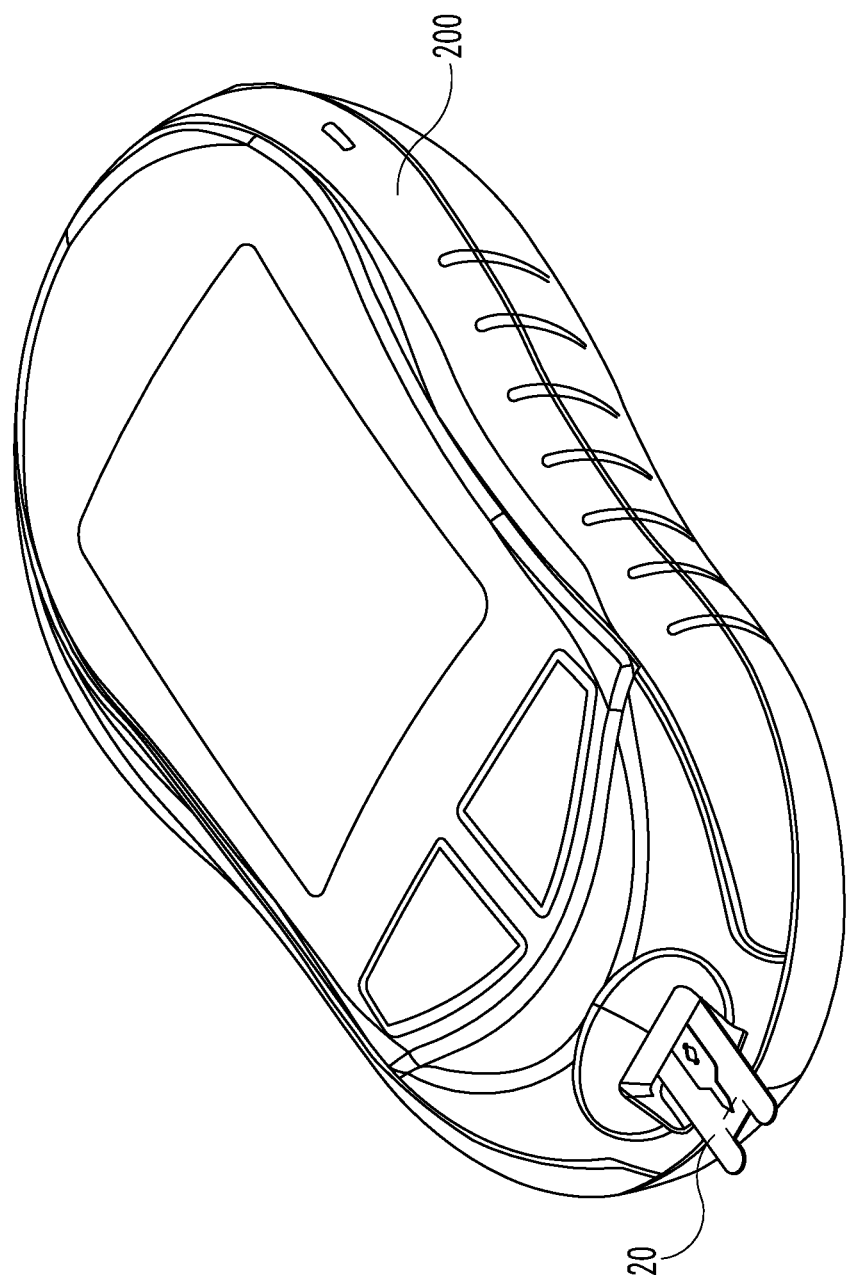
FIG. 7 is a top perspective view of the FIG. 1 device extending from a test meter.

In another embodiment, the integrated lancing test strip 20 is used with a housing having an opening or a mechanism sized to express body fluid to an incision site when pressed against skin. Some other examples of mechanisms sized to express body fluid to an incision site are a finger cone or a ring attached to the housing at the opening. In yet another embodiment illustrated in FIG. 7, the integrated lancing test strip 20 is used with a test meter 200. Beneficially, as the integrated lancing test strip 20 is pressed against skin, the skin is stretched before the lancet 22 forms an incision in skin. Therefore, depression of the skin by a lancet tip and correspondingly an uncertain incision depth are avoided with the first skin contacting tab 42 and the second skin contacting tab 44. Moreover, the lancet 22 forms an incision in skin to an accurate depth for each lancing event with the first skin contacting tab 42 and the second skin contacting tab 44. In other words, the first skin contacting tab 42 and the second skin contacting tab 44 ensure reproducibility of an accurate incision depth by the lancet 22.

Figure 6:
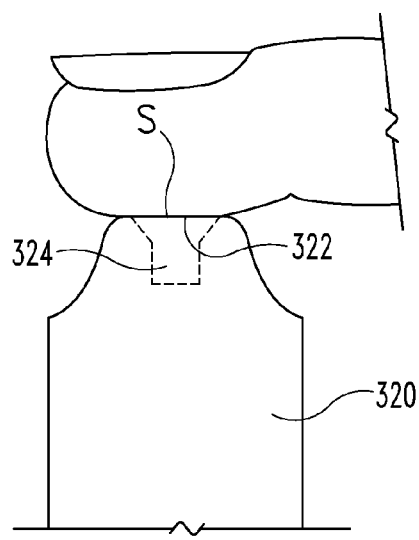
FIG. 6 is a top view of a prior art integrated lancet testing device pressed against a finger of a user.

The operation of a prior art test strip 320 pressed against a finger is illustrated in FIG. 6. Test strip 320 includes a substantially straight front end 322 which contacts a finger to flatten skin S. Test strip 320 includes a test area 324. Front end 322 is pressed against a finger therefore skin S is not bulged towards test area 324 and body fluid is not expressed to skin S. Moreover, skin S is not stretched taut by the substantially straight front end 322 therefore the pricking depth cannot be regulated and depression of skin S may not be avoided.

Figure 4:
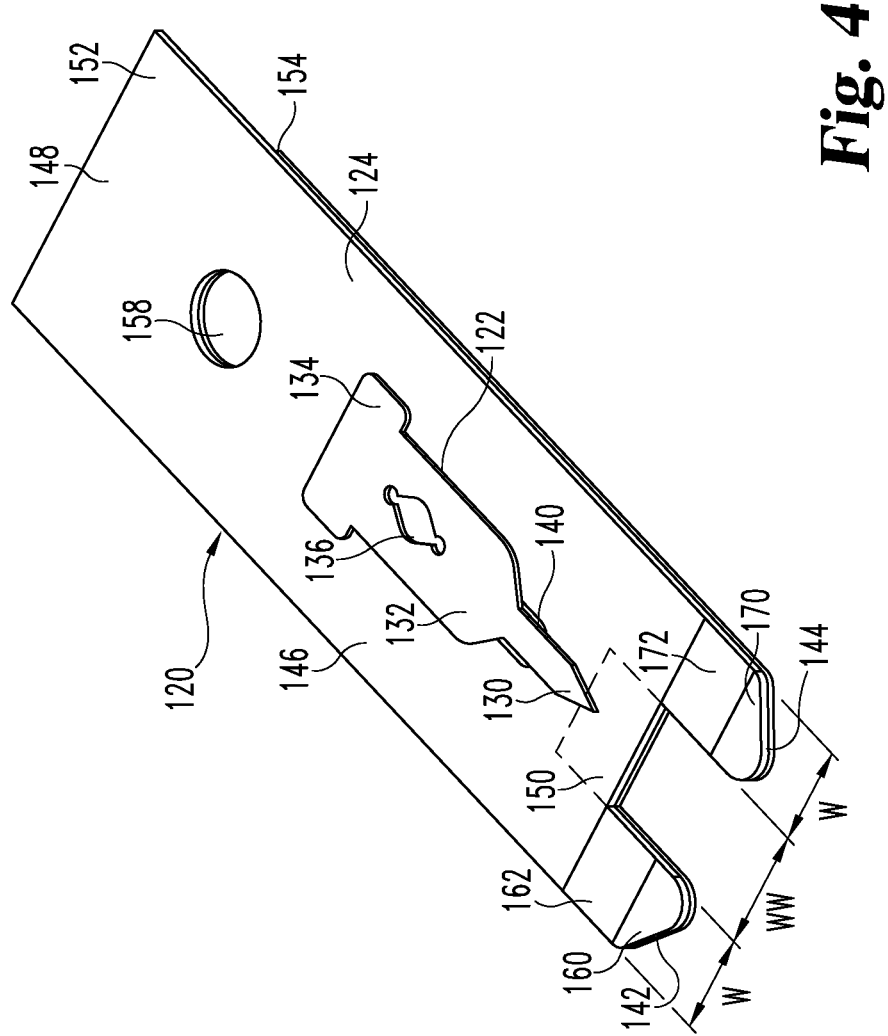
FIG. 4 is a top perspective view of an alternate embodiment of an integrated lancet testing device.
Figure 5:
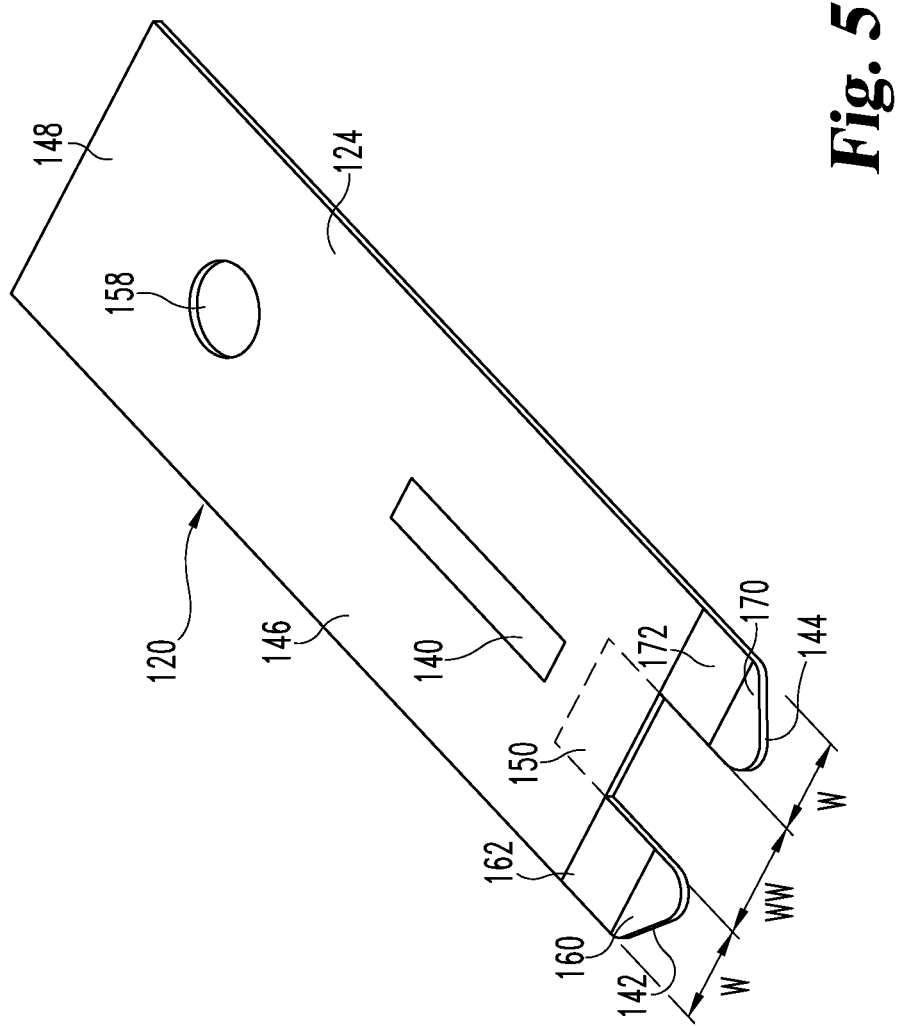
FIG. 5 is a back perspective view of the FIG. 4 device with the lancet.

An integrated lancing test strip or device 120 according to another embodiment will be described with reference to FIGS. 4 and 5. Integrated lancing test strip 120 is configured to stabilize the skin near an incision site, form an incision in skin, collect a body fluid sample from the incision, and analyze the body fluid sample. As should be recognized from these figures, integrated lancing test strip 120 shares a number of features in common with integrated lancing test strip 20 illustrated in FIGS. 1, 2, and 3. Therefore for the sake of brevity, common features from the integrated lancing test strip 120 and the integrated lancing test strip 20 will not be discussed. Like test strip 24, test strip 124 includes a first skin contacting tab 142 and a second skin contacting tab 144.

The first skin contacting tab 142 has a first skin contacting portion 160 that is configured to contact skin near an incision site. As illustrated, first skin contacting portion 160 is triangular in shape. The first skin contacting tab 142 also includes a leg portion 162 next to the first skin contacting portion 160. The second skin contacting tab 144 includes a second skin contacting portion 170 that is configured to contact skin near an incision site. The second skin contacting portion 170 is triangular in shape. The second skin contacting tab 144 includes a leg portion 172 next to second skin contacting portion 170. In one form, first skin contacting portion 160 and second skin contacting portion 170 each have a width, W, of approximately 3.25 millimeters. In one embodiment, test area 150 has a width, WW, of approximately 2.5 millimeters. Test strip 24 in one embodiment has a thickness of about 0.4 to 0.8 millimeters.

The operation of integrated lancing test strip 120 is similar to integrated lancing test strip 20. First skin contacting portion 160 and second skin contacting portion 170 are pressed against skin. The skin is stretched between first skin contacting portion 160 and second skin contacting portion 170. The skin between first skin contacting portion 160 and second skin contacting portion 170 is also bulged towards a test area 150 to express a bodily fluid sample. First skin contacting portion 160 and second skin contacting portion 170 are sized such that the incision remains open once it is formed by a lancet 122. Next an incision in skin is formed with a lancet tip 130. Lancet tip 130 pierces the skin without depressing the skin between the first skin contacting portion 160 and second skin contacting portion 170. Therefore an incision in skin to an accurate depth can be formed. The test area 150 is configured to collect a body fluid sample.

It should be appreciated that the integrated lancing test strip 20 and the integrated lancing test strip 120 can include combinations of the above-mentioned components in addition to other components. For example, the integrated lancing test strip 20 and the integrated lancing test strip 120 can include bendable wicking flags and the like that also contact the skin during sampling.

In the illustrated skin contacting portions, the skin contacting portions have a semi-circular or a triangular shape, but the skin contacting portions may be shaped differently in other embodiments. It should be recognized that the skin contacting portions can take different forms in other embodiments. For example, the skin contacting portions can be rectangular, square, oval, or polygonal.

It should be appreciated that the integrated lancing test strip 20 and the integrated lancing test strip 120 can include either photometric or electrochemical test strips.

As used in the specification and claims, the following definitions apply:

The term "lancet" is used in a broader sense and is meant to include any sharp and/or pointed structure for cutting incisions in tissue, such as a needle, blade, knife, scalpel, and the like. The lancet can be, whole or in part, hollow and/or solid. The lancet can be round, flat and/or have other cross-sectional shapes. Further, the lancet can have a single cutting surface or multiple cutting surfaces. The lancet can also be a microsampler.

The language used in the claims and specification is to only have its plain and ordinary meaning, except as explicitly defined above. The words in the above definitions are to only have their plain and ordinary meaning. Such plain and ordinary meaning is inclusive of all consistent dictionary definitions from the most recently published Webster's dictionaries and Random House dictionaries.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A test strip, comprising:
a body including a front edge, said body defining a passageway open at the front edge and extending from the front edge in a first, inward direction to a test area;
a reagent located in the test area;
a first skin contacting tab configured to contact skin near an incision site, said first skin contacting tab being substantially flat and extending from the front edge in a second, outward direction opposite to the inward direction; and
a second skin contacting tab configured to contact skin near an incision site, said second skin contacting tab being substantially flat and extending from the front edge in the second, outward direction opposite to the inward direction, the front edge extending between the first and second skin contacting tabs, said second skin contacting tab being coplanar with said first skin contacting tab, wherein said first skin contacting tab and said second skin contacting tab are spaced from each other a distance sufficient to stretch the skin between said first skin contacting tab and said second skin contacting tab when the test strip is pressed against the skin,
said body comprising a first panel overlying a second panel, the passageway extending between the first and second panels in the first direction from the front edge to the test area, each of the first and second panels including substantially flat, first and second skin contacting tabs extending from the front edge in the second, outward direction.

2. The test strip of claim 1, wherein:
said first skin contacting tab includes a first skin contacting portion connected to a first leg portion,
said second skin contacting tab includes a second skin contacting portion connected to a second leg portion, said first skin contacting portion and said second skin contacting portion are configured to stretch the skin positioned between said first skin contacting tab and said second skin contacting tab.

3. The test strip of claim 2, wherein said first skin contacting portion and said second skin contacting portion have mutually-facing rounded shapes positioned away from said body.

4. The test strip of claim 3, wherein the mutually-facing rounded shapes of said first and second skin contacting portions have an approximate radius of 1.6 millimeters.

5. The test strip of claim 4, wherein said test area and the front edge each have a width of approximately 2.5 millimeters.

6. The test strip of claim 2, wherein said first skin contacting portion and said second skin contacting portion have mutually-facing portions positioned away from said body and angled inwardly in the direction of the body.

7. The test strip of claim 1, further comprising:
a lancet coupled to said test strip to form an integrated lancet test strip, the lancet having a first position extending outwardly in the second direction from the front edge of said body between said first and second skin contacting tabs a distance sufficient to lance skin pressed against and stretched by said skin contacting tabs, and a second position withdrawn into said body.

8. The test strip of claim 7 further comprising a housing coupled to said test strip.

9. A method of using the test strip of claim 1, comprising:
positioning the first skin contacting tab and the second skin contacting tab of said test strip over an incision site on skin;
pressing said first skin contacting tab and said second skin contacting tab of said test strip against the skin to cause the skin to bulge towards the test area on said test strip; and
stretching the skin between said first skin contacting tab and said second skin contacting tab of said test strip.

10. The method of claim 9, further comprising forming an incision in skin with a lancet.

11. The test strip of claim 1 in which said body and said first and second skin contacting tabs comprise a single, integral layer.

12. The test strip of claim 7 in which said body and said first and second skin contacting tabs comprise a single, integral layer.

* * * * *

UNITED STATES PATENT AND TRADEMARK OFFICE
CERTIFICATE OF CORRECTION

PATENT NO.       : 9,475,044 B2                          Page 1 of 1
APPLICATION NO.  : 13/273409
DATED            : October 25, 2016
INVENTOR(S)      : Michael Keil It is certified that error appears in the above-identified patent and that said Letters Patent is hereby corrected as shown below:

On the Title Page

Please replace Assignee (73) from "Roche Diagnostics Operations, Inc." with --Roche Diabetes Care, Inc.--

Signed and Sealed this
Twenty-fifth Day of April, 2017

Michelle K. Lee
*Director of the United States Patent and Trademark Office*